US008315450B2

(12) United States Patent
Quigley

(10) Patent No.: US 8,315,450 B2
(45) Date of Patent: Nov. 20, 2012

(54) METHOD AND SYSTEM FOR DISPLAY OF MEDICAL IMAGE DATA

(75) Inventor: Mark F. Quigley, Bowie, MD (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1523 days.

(21) Appl. No.: 11/280,051

(22) Filed: Nov. 16, 2005

(65) Prior Publication Data

US 2006/0119623 A1 Jun. 8, 2006

Related U.S. Application Data

(60) Provisional application No. 60/630,724, filed on Nov. 24, 2004.

(51) Int. Cl.
*G06K 9/00* (2006.01)
(52) U.S. Cl. .......... 382/131; 600/407; 600/410
(58) Field of Classification Search .......... 600/407–410, 600/430, 437, 473–480; 345/7, 72, 74, 418–427; 348/36, 37; 382/128–136
See application file for complete search history.

(56) References Cited

U.S. PATENT DOCUMENTS

| | | | | |
|---|---|---|---|---|
| 5,431,161 | A * | 7/1995 | Ryals et al. | 600/425 |
| 5,845,639 | A * | 12/1998 | Hochman et al. | 600/407 |
| 6,505,063 | B2 * | 1/2003 | Van Den Brink et al. | 600/411 |
| 6,690,386 | B2 * | 2/2004 | Edelson et al. | 345/634 |
| 6,765,566 | B1 * | 7/2004 | Tsao | 345/419 |
| 6,766,064 | B1 * | 7/2004 | Langan et al. | 382/274 |
| 7,177,452 | B2 * | 2/2007 | Wong et al. | 382/128 |
| 7,259,729 | B2 * | 8/2007 | Shastri et al. | 345/1.3 |
| 7,339,587 | B2 * | 3/2008 | Kropfeld | 345/424 |
| 7,525,554 | B2 * | 4/2009 | Morita et al. | 345/619 |
| 7,590,440 | B2 * | 9/2009 | Lau et al. | 600/413 |
| 7,620,227 | B2 * | 11/2009 | Gering et al. | 382/128 |
| 7,715,901 | B2 * | 5/2010 | Salomon et al. | 600/411 |
| 2005/0240253 | A1 * | 10/2005 | Tyler et al. | 607/134 |
| 2006/0161218 | A1 * | 7/2006 | Danilov | 607/45 |
| 2006/0241718 | A1 * | 10/2006 | Tyler et al. | 607/45 |

OTHER PUBLICATIONS

Lucien M. Levy; MR Identification of Chiari Pathophysiology by Using Spatial and Temporal CSF Flow Indices and Implication for Syringomyelia; American Jour. of Neuroradiology 24:165-166, Feb. 2003.
Victor M. Haughton et al; Peak Systolic and Diastolic CSF Velocity in the Foramen Magnum in Adult Patients with Chiari I Malformations and in Normal Control Participants; AJNR Am J Neuroradiol 24:169-176, Feb. 2003.

* cited by examiner

*Primary Examiner* — Sanjay Cattungal
(74) *Attorney, Agent, or Firm* — Quarles & Brady, LLP; Jack M. Cook

(57) ABSTRACT

Multiple cardiac gated, flow encoded, 2DFT MR images are acquired transversely in the vicinity of the foramen magnum of a subject. For each resulting 2D image parametric images depicting cephalad CSF flow caudad CSF flow and CSF throughput are reconstructed and displayed. CSF velocity images are reconstructed at successive cardiac phases and CSF flow velocity at each voxel therein is plotted as a function of cardiac phase. Cumulative flow images are also reconstructed and successive voxel values therein are also plotted. A link is established between displayed plotted curves and locations in the parametric images to facilitate diagnosis of Chiari I disease.

25 Claims, 10 Drawing Sheets

METHOD AND SYSTEM FOR DISPLAY OF MEDICAL IMAGE DATA

CROSS-REFERENCE TO RELATED APPLICATIONS

This application is based on U.S. Provisional Patent Application Ser. No. 60/630,724 filed on Nov. 24, 2004 and entitled "METHOD AND SYSTEM FOR DISPLAY OF MEDICAL IMAGE DATA."

BACKGROUND OF THE INVENTION

The field of the invention is nuclear magnetic resonance ("NMR") imaging methods and systems. More particularly, the invention relates to the display of NMR image data indicative of flow, or motion over an acquisition time period to facilitate diagnosis of disease.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$ $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

MR methods have been developed that encode motion into the phase of the acquired signal as disclosed in U.S. Pat. No. Re. 32,701. These form a class of techniques known as phase contrast (PC) methods. Currently, most PC techniques acquire two images, with each image having a different sensitivity to the same velocity component. Images are then obtained by forming either the phase difference or complex difference between the pair of velocity-encoded images. Phase contrast techniques have been extended so that they are sensitive to velocity components in all three orthogonal directions, and the technique has been extended to so-called projection reconstruction MRI as disclosed in U.S. Pat. No. 6,188,922.

The "Chiari Malformation" is a birth defect occurring in around 1 in 2000 births. Referring particularly to FIG. 5, it is characterized by the descent of part of the cerebellum (the 'tonsils' 10) through the foramen magnum. The foramen magnum is the largest opening into the cranial vault at the base of the skull. The spinal cord, vertebral arteries and their anterior and posterior spinal branches enter the skull through this opening. The degree of descent of the tonsils 10 ranges up to 15 mm or more, with 3 mm generally being considered the point at which the patient is considered to have a malformation. (Such a condition is known as a Chiari I). Roughly half of the population with a Chiari malformation never exhibit any symptomatology. The onset of symptoms usually ranges from infancy to the mid-20's, although older patients developing symptoms is not uncommon.

The symptomatic malformation is characterized by damage to the upper spinal cord, with a syrinx (a cavity within the cord) developing about half the time. Because both the cranium and spine are rigid structures, blood pumped into the brain displaces the same volume of CSF down into the spine. Conversely, when blood leaves the brain during diastole, CSF returns to the cranium. Current theory holds that because the tonsils 10 obstruct part of the subarachnoid space, CSF flow is impeded, resulting in higher pressures within the spinal cavity. One variation on this theory is that the tonsils 10 act in the manner of pistons, creating pressure waves, which damage the spinal cord. In any event, higher than normal pressure have been measured in symptomatic Chiari patients with a manometer inserted into the spinal cavity.

Treatment is surgical, usually involving removing the tonsils 10 and widening the posterior part of the foramen magnum opening to allow greater CSF flow. With the advent of MRI, diagnosis of the degree of the descent of the tonsils 10 is easily measured, and this measurement is the current marker used for diagnosis. However, there seems to be very little correlation between the degree of tonsil descent and the severity of symptoms, nor has it been possible to predict the outcome of corrective surgery based on such anatomic MR images. In fact Chiari-like spinal cord damage occurs even with no descent of the tonsils at all. This condition is called a Chiari 0. Symptoms improve or disappear with the same surgical procedures used in Chiari I patients.

It seems reasonable to conclude that occlusion or blockage of flow caused by the tonsils 10 should lead to abnormal CSF flow velocities, and that diagnostic techniques based on measurement of CSF flow velocity might lead to better results. Since 1991, there have been roughly 30 studies using phase contrast MR to measure instantaneous CSF flow velocity and volume over the course of the cardiac cycle. These studies have yielded inconsistent and often contrary results. These have arisen due to uncorrected aliasing, venous or arterial flow being mistaken for cerebrospinal fluid flow, and the universal practice in these studies of determining flow parameters by averaging data for all CSF velocities at a particular point in time.

More recently, the peak CSF flow velocity at locations in the foramen magnum was used as an index for evaluating patients as described by Haughton et al "Peak Systolic And Diastolic CSF Velocity In The Foramen Magnum In Adult Patients With Chiari I Malformations And In Normal Control Participants", *American Journal of Neuroradiology*, 24:169-176, February 2003. Bernoulli's principle states that if a given (incompressible) volume of fluid moves from an area of large cross-section to an area of smaller cross-section, the velocity will increase. Thus, it would seem reasonable that Chiari I patients, in which the cross-section of the subarachnoid space is decreased due to the presence of tonsils 10 should exhibit higher velocities then normal patients. Haughton et al measured the extreme velocity by inspecting individual voxels, yielding peak velocity measurements at each point in the cardiac cycle that was measured. In general, Chiari I patients did show higher extreme localized velocity measurements, but this was not a universal finding, mainly due to undetected aliasing in the majority of the patients which had the effect of lowering the measured extreme velocities.

SUMMARY OF THE INVENTION

The present invention is a method and system for assisting in the diagnosis of disease using a data set containing spatially localized measurements acquired over a period of time. More specifically, the invention includes: displaying a spatial image using measurements in the data set acquired at a selected time; displaying temporal plots of measurements in the data set as a function of time for spatial locations in the spatial image; selecting a spatial location in the spatial image and highlighting the corresponding displayed temporal plot, or designating a point on one of the displayed temporal plots and updating the spatial image with measurements acquired at the time indicated by the designated point, or selecting a displayed temporal plot and highlighting the corresponding spatial location on the displayed spatial image.

A general objective of the invention is to provide a tool which enhances the diagnostic value of a data set which includes spatially localized measurements acquired over time. The reconstructed image may overlay an anatomic image of the patient to relate measurements to the anatomy and the plots indicate the change in measured values at specific locations over the acquisition time period. The image contains spatial location information at one point in time, whereas the plots contain temporal information. By creating a spatial-temporal mapping which links the two types of data, the diagnostician is better able to comprehend both the spatial and temporal nature of the acquired measurements.

A more specific objective of the invention is to provide a tool for the diagnosis of Chiari Malformation. The spatial-temporal mapping provided by the present invention enables velocities measured at spatial locations in the foramen magnum to be displayed at different times during the patient's cardiac cycle. It is apparent from the displayed spatial image and the displayed temporal plots that preserving both the spatial and temporal information with the velocity measurements reveals that the effects of Chiari Malformation is far more complex than previously recognized. It is not just the spatial location of a measured velocity or peak velocity that has diagnostic value, but also when the peak velocity occurs relative to surrounding locations.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 1:
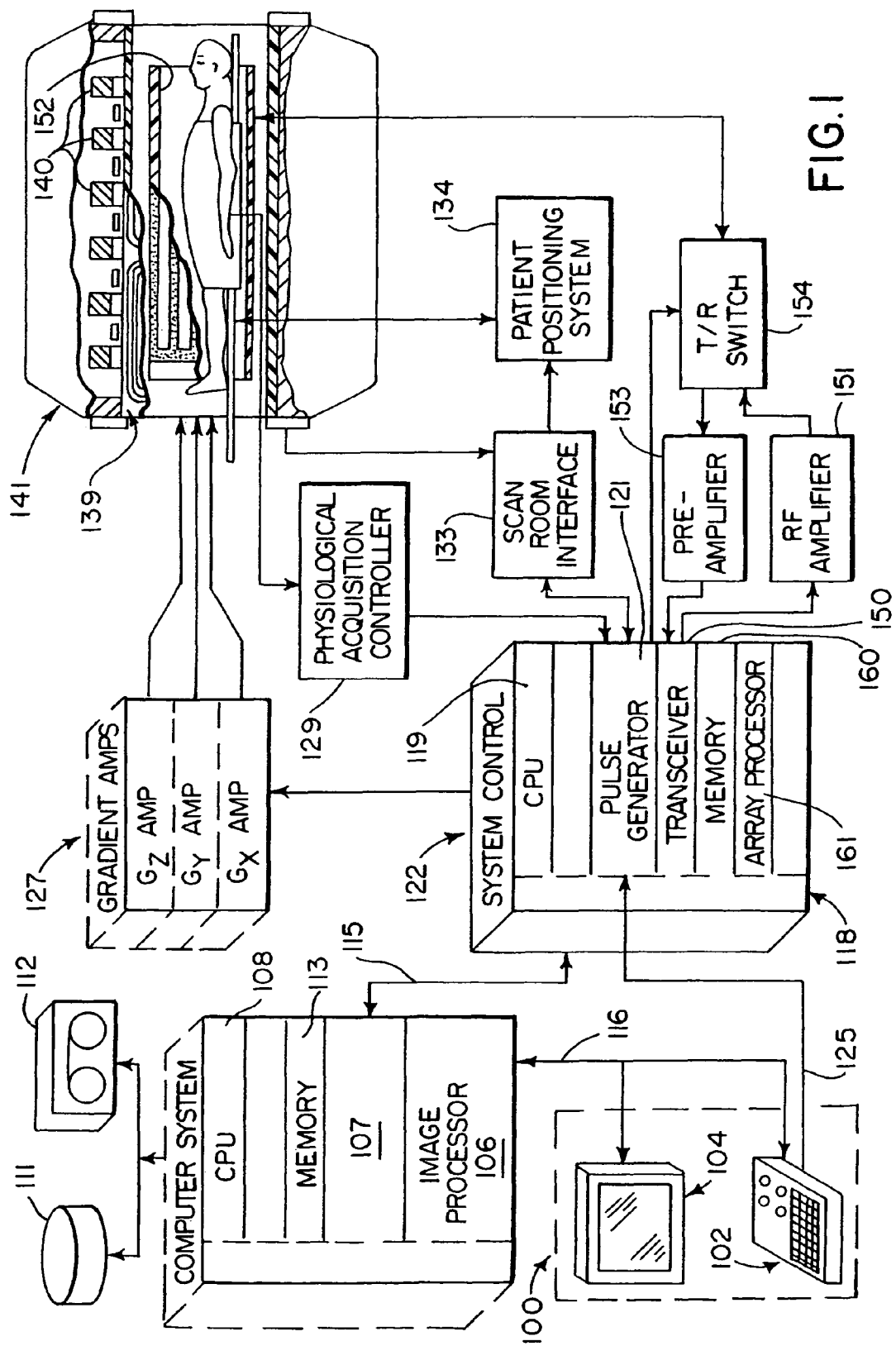
FIG. 1 is an electrical block diagram of an MRI system used to acquire the data set employed in the preferred embodiment of the invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122 through a backplane 118. When the scan is completed and an entire array of data has been acquired in the memory module 160, an array processor 161 operates to reconstruct one or more images as will be described below. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
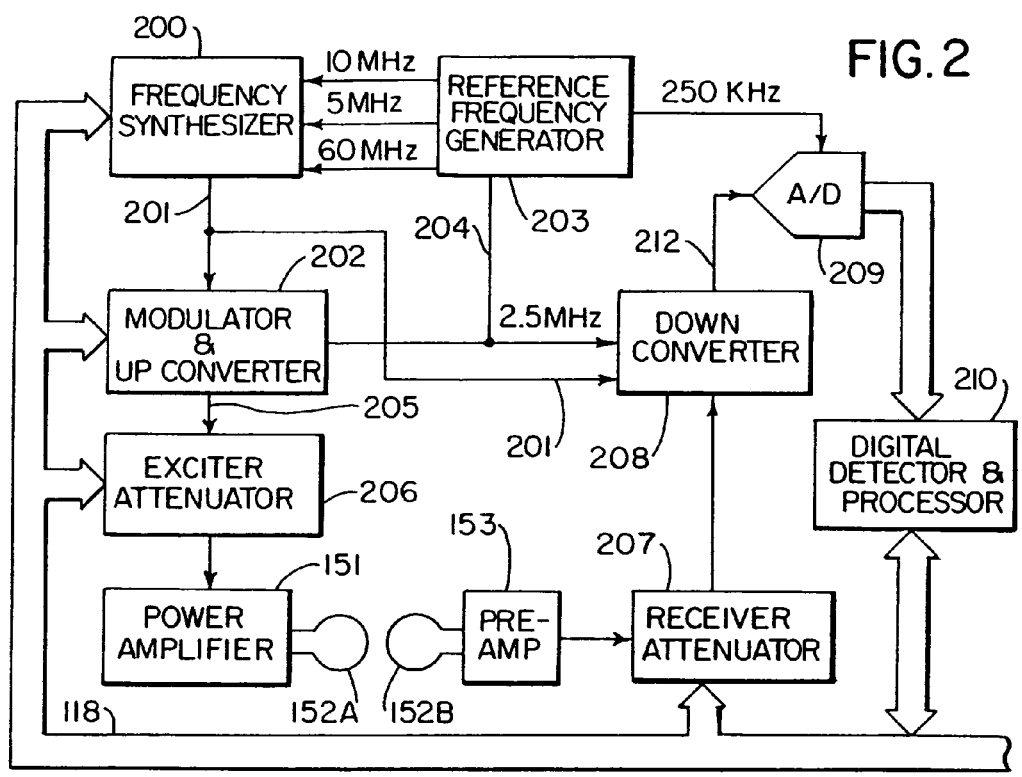
FIG. 2 is a transceiver which forms part of the MRI system of FIG. 1.

Referring particularly to FIGS. 1 and 2, the transceiver 150 produces the RF excitation field B1 through power amplifier 151 at a coil 152A and receives the resulting signal induced in a coil 152B. As indicated above, the coils 152A and B may be separate as shown in FIG. 2, or they may be a single whole-body coil as shown in FIG. 1. The base, or carrier, frequency of the RF excitation field is produced under control of a frequency synthesizer 200 which receives a set of digital signals from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from the pulse generator module 121. The signal R(t) defines the envelope of the RF excitation pulse to be produced and is produced in the module 121 by sequentially reading out a series of stored digital values. These stored digital values may, in turn, be changed from the operator console 100 to enable any desired RF pulse envelope to be produced.

The magnitude of the RF excitation pulse produced at output 205 is attenuated by an exciter attenuator circuit 206 which receives a digital command from the backplane 118. The attenuated RF excitation pulses are applied to the power amplifier 151 that drives the RF coil 152A.

Referring still to FIG. 1 and 2 the signal produced by the subject is picked up by the receiver coil 152B and applied through the preamplifier 153 to the input of a receiver attenuator 207. The receiver attenuator 207 further amplifies the signal by an amount determined by a digital attenuation signal received from the backplane 118.

The received signal is at or around the Larmor frequency, and this high frequency signal is down converted in a two step process by a down converter 208 which first mixes the NMR signal with the carrier signal on line 201 and then mixes the resulting difference signal with the 205 MHz reference signal on line 204. The down converted NMR signal is applied to the input of an analog-to-digital (A/D) converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output through backplane 118 to the memory module 160 where they are employed to reconstruct an image.

The 2.5 MHz reference signal as well as the 250 kHz sampling signal and the 5, 10 and 60 MHz reference signals are produced by a reference frequency generator 203 from a common 20 MHz master clock signal.

Figure 3:
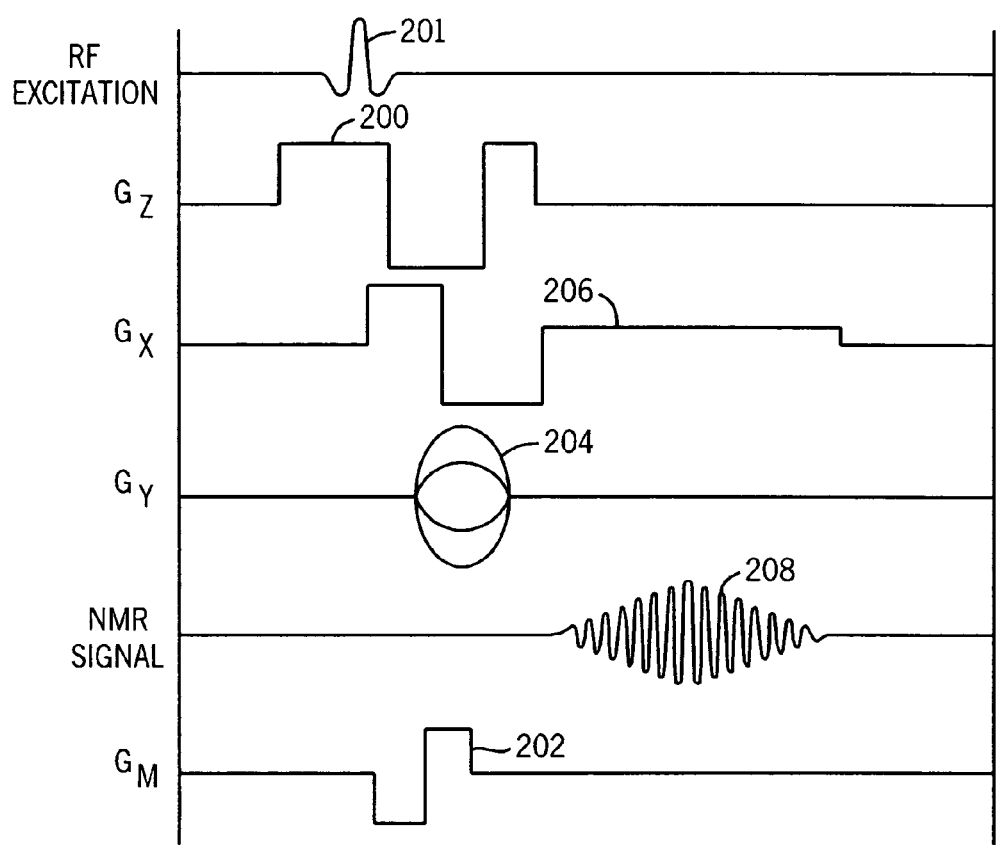
FIG. 3 is a graphic representation of a pulse sequence used by the MRI system of FIG. 1 to acquire the data set.

Referring particularly to FIG. 3, a 2DFT phase contrast pulse sequence is employed to acquire the flow measurements. The pulse sequence includes a slice select gradient $G_z$ pulse 200 directed along the z-axis that is substantially parallel to the patient's spinal column. It is produced concurrently with a selective RF excitation pulse 201. A bipolar, motion encoding gradient pulse 202 is then applied to impart a phase proportional to spin velocity along the direction of the motion encoding gradient $G_m$. In the preferred embodiment $G_m$ is directed along the z-axis and it thus measures velocity along the direction of the patient's spinal column.

Each pulse sequence also includes a phase encoding gradient pulse 204 directed along the y-axis. As is known in the art, the pulse sequence is repeated and the phase encoding pulse 204 is stepped through a set of values to sample k-space in the prescribed manner. A readout gradient pulse 206 is directed along the x-axis is then produced, and at the same time an NMR gradient-echo signal 208 as acquired.

In the preferred embodiment the gradient pulses in the pulse sequence are set to select a 5 mm thick slice and a 256×256 voxel 2D image is acquired. For an adult patient the field of view of the image is 24 cm by 24 cm and the first moment of the motion encoding gradient 202 is set to a VENC of 10 cm/sec. As is well known in the art, the pulse sequence is repeated twice at each phase encoding with the polarity of the motion encoding gradient lobes 202 reversed. This enables phase shifts caused by factors other than spin motion to be subtracted out, or nulled.

Figure 4:
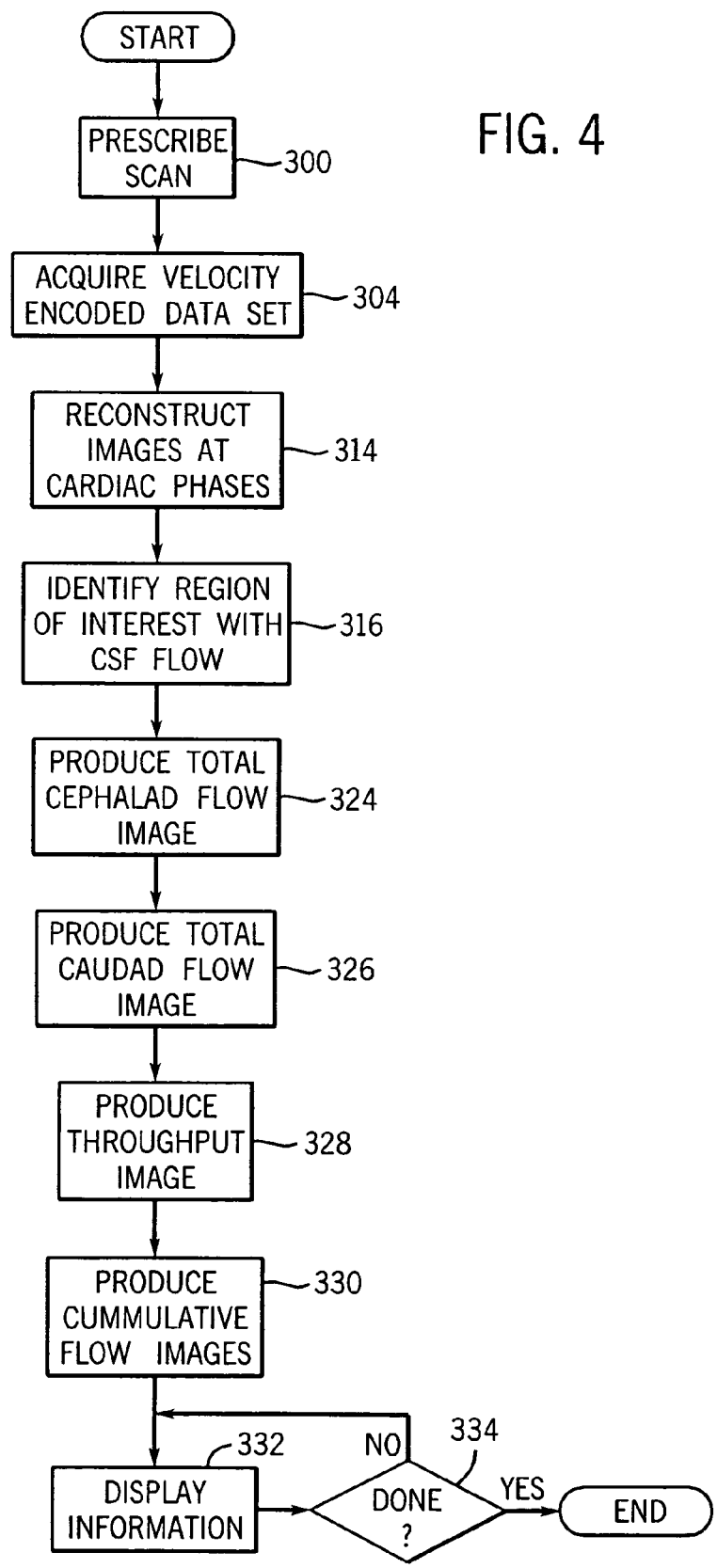
FIG. 4 is a flow chart of the steps performed when practicing a preferred embodiment of the invention.
Figure 5:
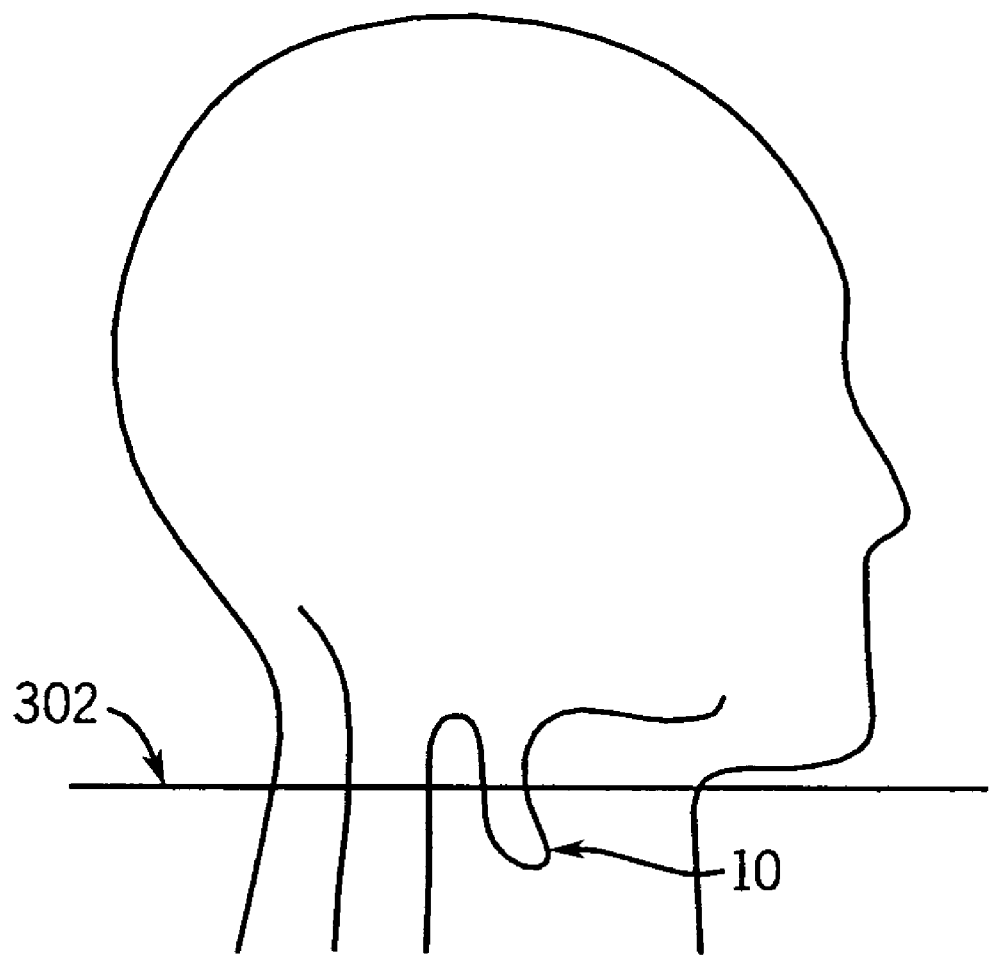
FIG. 5 is a pictorial representation of a subject having Chiari Malformation.

Referring particularly to FIG. 4, the first step in the procedure for examining CSF flow in the foramen magnum is to prescribe an MRI scan as indicated at process block 300. This includes performing an initial MRI scan to acquire a mid-sagittal image at the base of the subject's skull. As shown in FIG. 5, this enables the location of a transverse plane 302 at the z-axis location of the foramen magnum to be determined. One transverse 2D slice image is prescribed at this location and up to three transverse slices are prescribed to each side to ensure the necessary data is acquired.

Figure 6:
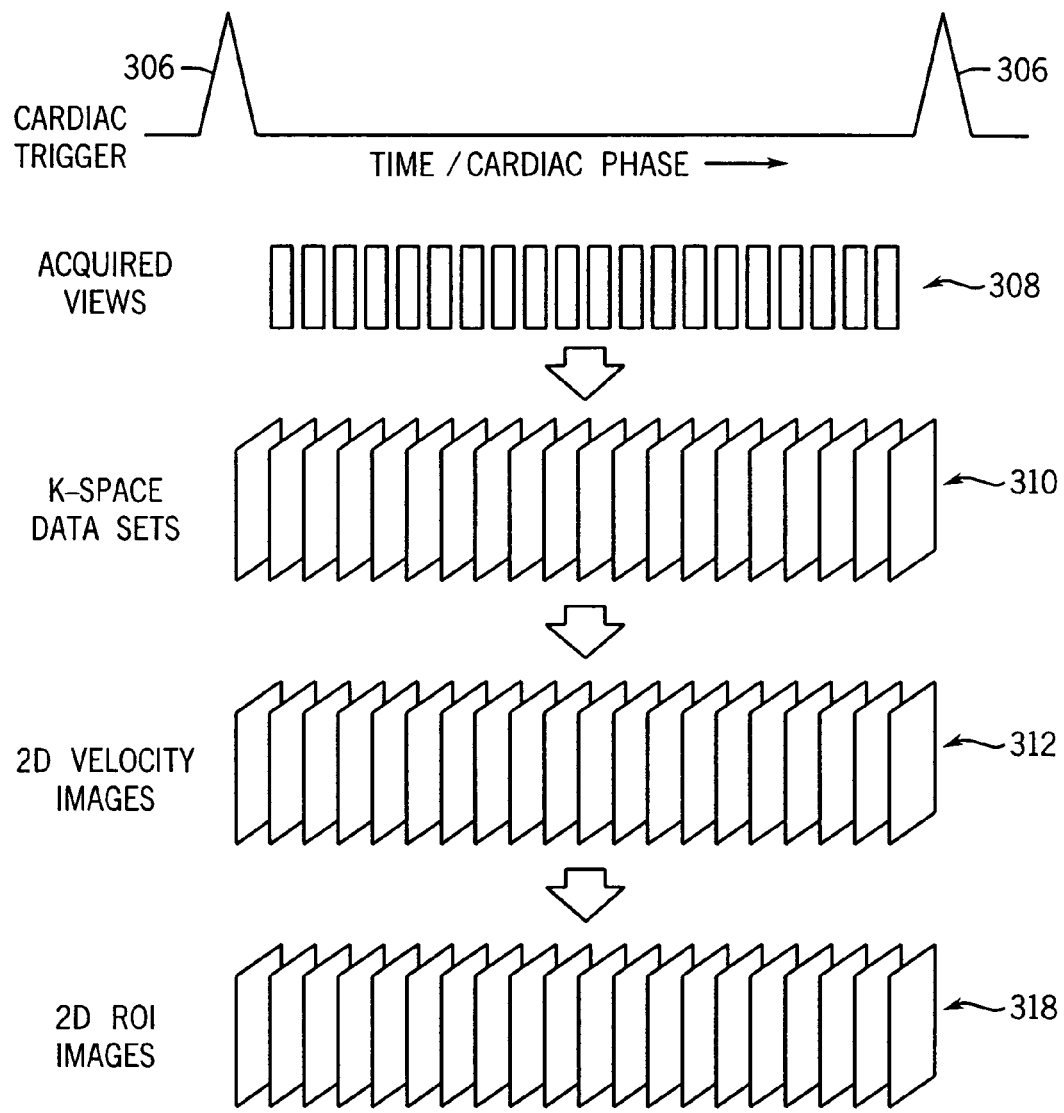
FIG. 6 is a pictorial representation of the data which is acquired and processed when practicing the method of FIG. 4.

As indicated at process block 304 in FIG. 4, the next step is to acquire the velocity encoded data set using the above-described pulse sequence. Referring particularly to FIG. 6, the data acquisition is cardiac gated by a cardiac trigger signal 306 produced at the beginning of each cardiac cycle. Shortly thereafter a series of 14 to 20 views 308 are acquired using the above-described pulse sequence at a single phase encoding value. Each acquired view 308 is stored in a corresponding one of 14 to 20 k-space data sets 310, and after 256 different phase encoded views are acquired (i.e., 256 heart beats) 14 to 20 complete 2D k-space data sets result. Each 2D k-space data set corresponds to a particular time, or cardiac phase, during a heart beat. It should be apparent that while only a single 2D slice is acquired at each cardiac phase in the preferred embodiment, it is also possible to acquire a 3D dataset. This can be accomplished by acquiring multiple 2D slices using the above described pulse sequence, or by using a 3D pulse sequence.

Referring to FIGS. 4 and 6, after the k-space data sets have been acquired they are used to reconstruct 14-20 2D images 312 as indicated at process block 314. This step includes performing a complex two-dimensional Fourier transformation on each 2D k-space data set and then calculating the phase $\phi$ at each image voxel from the quadrature complex components I and Q: $\phi = \tan^{-1} I/Q$. Phase shifts caused by factors other than spin motion are then nulled by subtracting the reference phase at the same voxel as discussed above.

As indicated above, the VENC of the motion encoding gradient 202 is set to 10 cm/sec. In an adult patient the velocity of spins in about 5% of the CSF image voxels will exceed this speed causing the phase φ of the NMR signal to wrap around and cause an inaccurate indication of spin velocity at that location. Such phase wrapping can be corrected by displaying the images and manually locating phase wrapped image voxels, or such phase wrapped voxels can be automatically detected and unwrapped using a method such as that disclosed by Lee A T, Pike G B, Pelc N J, "Three-Point Phase Contrast Velocity Measurements With Increased Velocity-To-Noise Ratio" Magnetic Resonance in Medicine, 1995, January, 33(1):122-6. See also U.S. Pat. No. 6,703,835 for a possible automatic unwrapping method.

Referring to FIG. 4, the next step indicated at process block 316 is to identify those voxels in the reconstructed velocity images 312 that correspond to CSF flow. This is the region of interest ("ROI") that is of clinical significance. Many voxels correspond to static tissues and these can be distinguished easily with a velocity threshold. The CSF voxels will reach a velocity in excess of 2.0 cm/sec. at some time during the cardiac cycle. Elimination of voxels corresponding to other flowing spins such as arterial or venous blood flow is a little more difficult since they will in all likelihood pass the velocity threshold test. However, over a cardiac cycle the flow through an artery or vein will be in one direction and the cumulative flow will be substantial. In contrast, CSF flow is typically in both directions during a cardiac cycle and the cumulative flow in either direction is small relative to venous or arterial cumulative flow, even if it is aliased.

Figure 7:
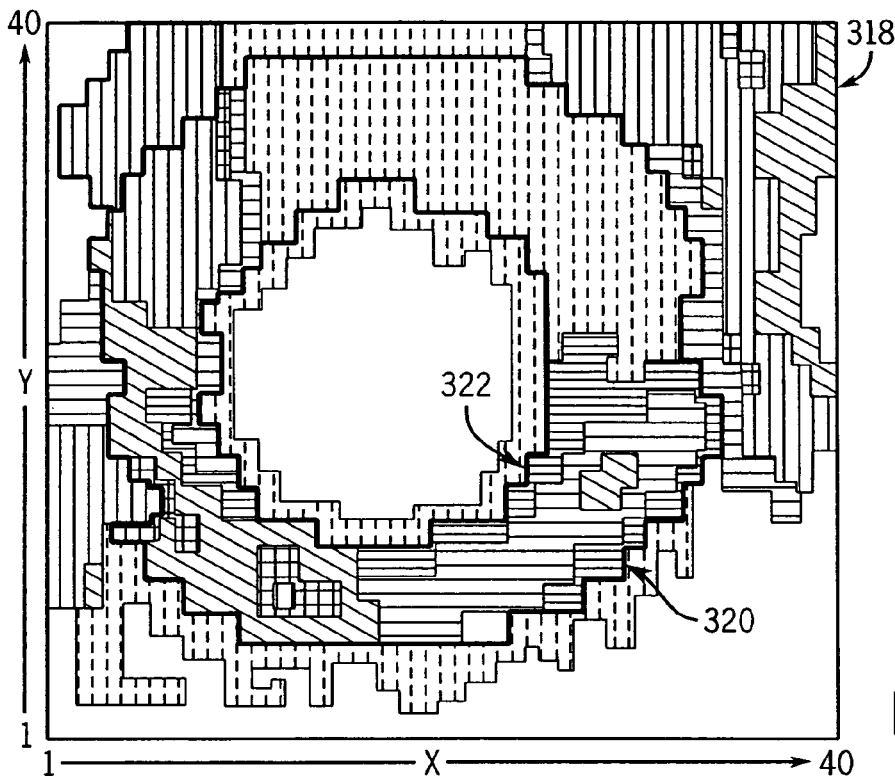
FIG. 7 is an image produced when practicing the method of FIG. 4.

As shown in FIG. 6, the result of this step is 14 to 20 ROI images 318, which depict a 40 by 40 voxel region that includes the flowing CSF. As shown in FIG. 7, the CSF ROI is outlined in these velocity images 318 as indicated at 320 and 322. Each voxel in the ROI images 318 has an identity (ID) determined by its x, y position in the 40 by 40 array of voxels. This identity (ID) corresponds to a physical, or anatomical, location in the subject.

There are a number of CSF flow parameters that are helpful in diagnosing the Chiari I condition. The 14 to 20 ROI images 318 are analyzed to produce a series of images which depict these parameters. Referring again to FIG. 4, the first parametric images produced at process block 324 measure the total cephalad CSF flow at a voxel during a cardiac cycle. This is determined for each voxel by summing all the positive velocity values in the 14 to 20 ROI images 318. The positive values indicate CSF flow into the cranium. The total is used to color modulate the voxel using the violet/blue/green/orange/yellow/red scheme for increasing values. Similarly, as indicated at process block 326, a total caudad CSF flow image is produced to indicate the amount of CSF flow out of the cranium at each ROI voxel during a complete heart cycle. This parameter is measured by summing all the negative velocities for a voxel in the 14 to 20 ROI images 318. Also, a throughput image is produced as indicated at process block 328. The throughput of each voxel is calculated by summing the absolute value of the voxels in all 14 to 20 velocity images produced throughout the cardiac cycle.

The three parametric images: total cephalad flow; total caudad flow; and throughput are each single images that reflect a total value at the end of a cardiac cycle. They do not reveal any information regarding CSF flow at any particular moment during the cardiac cycle.

As indicated at process block 330, a set of 14 to 20 cumulative flow images are produced next. A 40 by 40 voxel image is produced at successive cardiac phases by integrating, or summing, the velocities for each voxel therein up to that point in time/cardiac phase. Thus, a series of 14 to 20 images are produced which indicate the cumulative flow of CSF through each voxel therein at successive cardiac phases. As with the 14 to 20 ROI images 318 that indicate CSF flow velocity at each voxel during successive cardiac phases, the cumulative flow images contain temporal information that indicates how flow behaves during the cardiac cycle.

As indicated at process block 332 the information acquired during the scan and processed as described above is displayed in a unique manner to facilitate diagnosis of disease. This method will be discussed in more detail below. At some point as indicated by decision block 334, the user will indicate that the session is completed and the process will end.

Figure 8A:
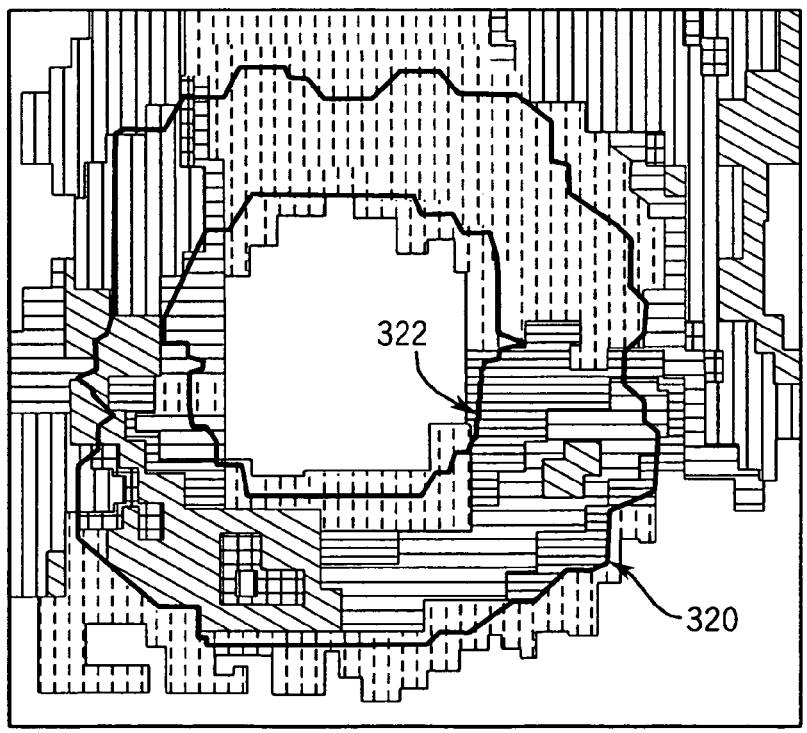
FIGS. 8A and 8B are images produced when practicing the method of FIG. 4.

One aspect of the present invention is the method used to display the above described information. The single parametric images (total cephalad flow, total caudad flow, throughput) can be displayed as a spatial image as illustrated in FIG. 8A, where the parameter value modulates the color of the voxel. The advantage of a spatial image is that it relates the measured parameter to the subject's anatomy. A similar spatial image can also be produced for CSF velocity or cumulative flow, however, if this is done one must select one image at a particular cardiac phase. The spatial depiction of information does not reveal temporal changes that occur during a cardiac cycle and that may be of diagnostic value.

Figure 8B:
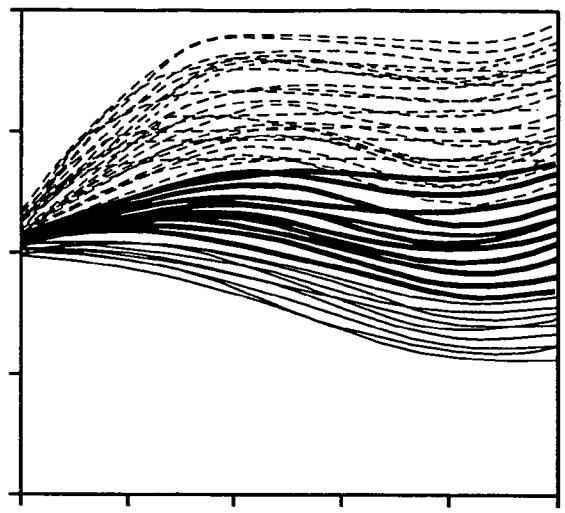
Figure 8C:
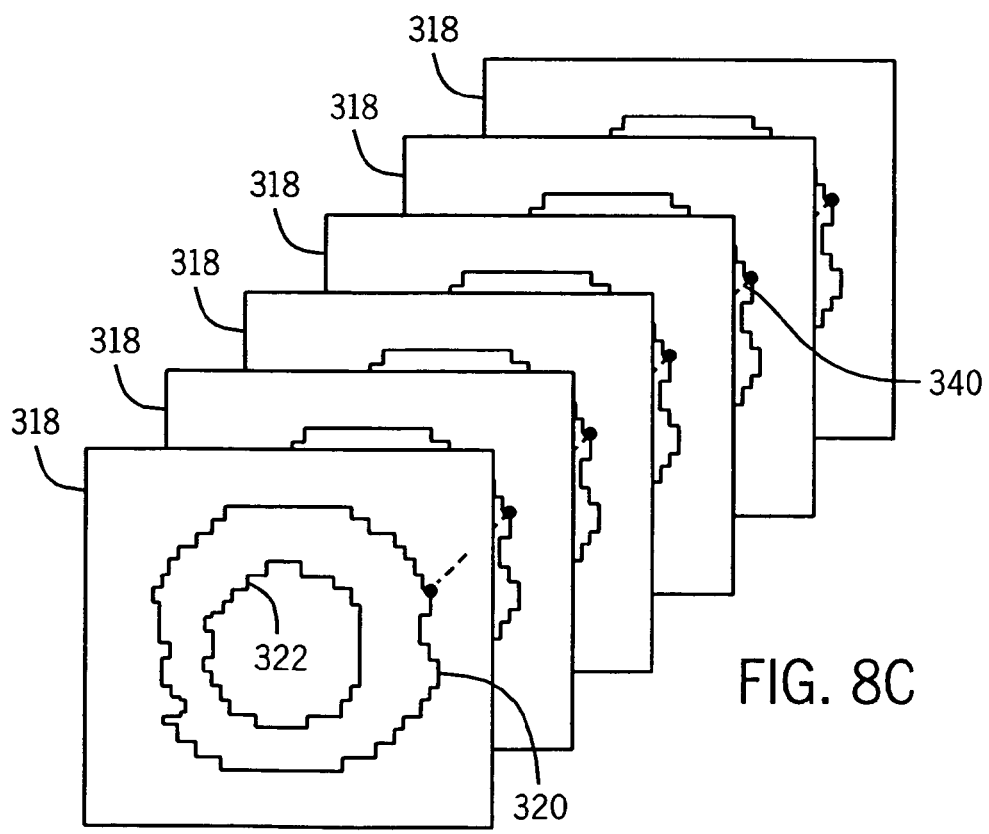
FIG. 8C is a pictorial representation of data extracted to form the image in FIG. 8B.

Temporal changes in CSF flow velocity and cumulative flow are depicted by plotting the parameter value as a function of cardiac phase, or time, for each image voxel as shown in FIG. 8B. As shown in FIG. 8C, for example, the CSF flow velocity data is plotted by reading successive values of a corresponding voxel from the 14 to 20 successive ROI velocity images 318 indicated by dashed line 340 and producing a graphic curve, or temporal plot, on the display of FIG. 8B with these values. This is repeated for each image voxel that is within the CSF outlines 320 and 322 to produce a large number of graphic curves on the display of FIG. 8B. Each graphic curve in the display of FIG. 8B thus depicts the changes that occur in the parameter value at one voxel during a cardiac cycle. While the graphic curves in the display of FIG. 8B show temporal changes in a parameter value, all spatial information is lost.

Figure 9:
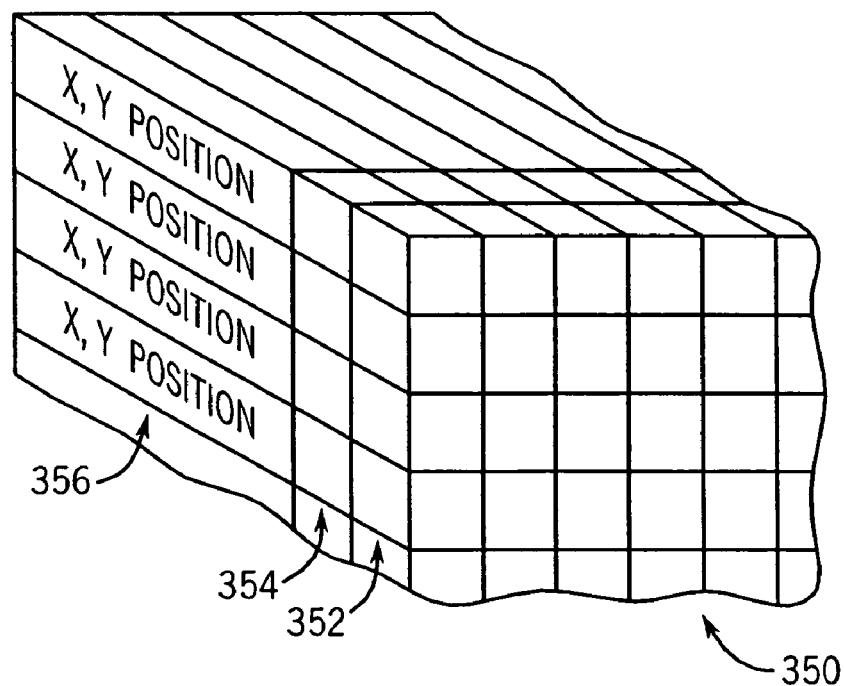
FIG. 9 is a pictorial representation of a data structure associated with the image of FIG. 8B.

To preserve spatial information in the curves of display 8B, spatial information is saved with each plotted curve. Referring particularly to FIG. 9, a graphic curve is produced on the display of FIG. 8B by setting the intensity level of appropriate voxels in a display memory 350. The display memory 350 is a three-dimensional array which stores for each voxel a value 352 which indicates whether or not the voxel is illuminated as part of a graphic curve. Another bit 354 indicates whether the voxel is highlighted or just illuminated and a field 356 stores the voxel ID, or x, y image location of the voxel that produced the graphic curve. As a result, each illuminated voxel in the graphic curves on the display of FIG. 8B has associated with it data which indicates whether or not the voxel should be illuminated, whether or not the voxel is highlighted and data which indicates the x, y location of the image voxel that produced the graphic curve. Each graphic curve is thus linked to a location in the spatial images. A voxel may be highlighted by either increasing its displayed intensity or color.

Figure 11:
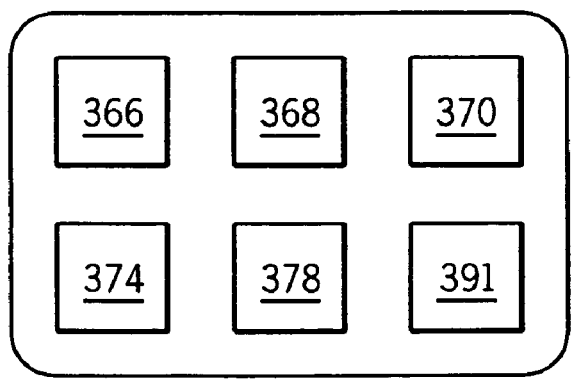
FIG. 11 is a pictorial representation of the display produced by the program of FIG. 10.
Figure 10:
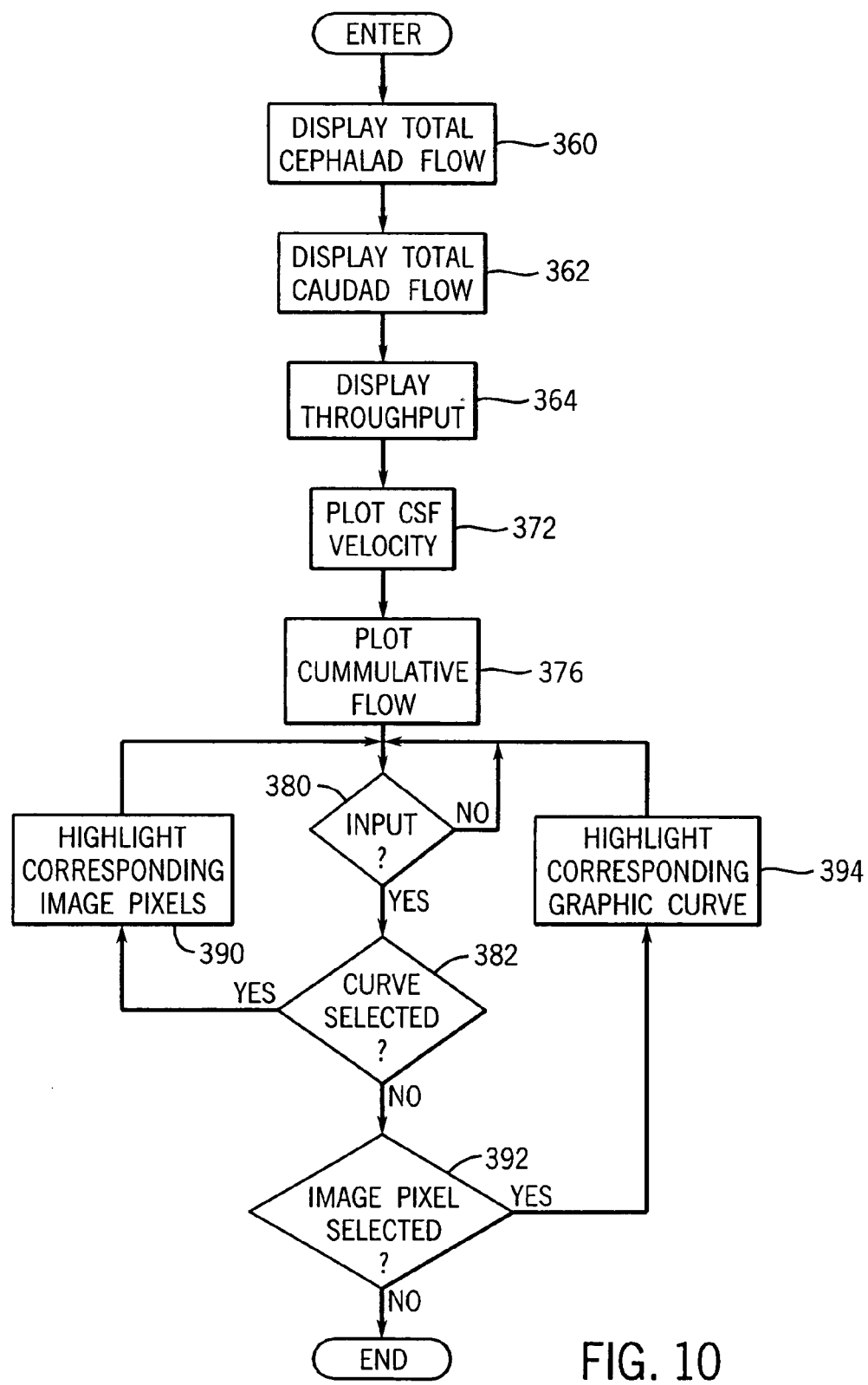
FIG. 10 is a flow chart of a display program which forms part of the method of FIG. 4.

The display process 332 in FIG. 4 will now be described in more detail with reference to FIG. 10. As indicated by process blocks 360, 362 and 364 the three spatial images of cephalad flow, caudad flow and throughput are displayed across the top of the display as shown at 366, 368 and 370 respectively in FIG. 11. The CSF voxels in the velocity images are plotted as indicated at process block 372 and the resulting graphic curves are displayed beneath the spatial images at 374. The CSF voxels in the cumulative flow image are also plotted as indicated at process block 376 and the resulting graphic curves are displayed beneath the spatial images at 378.

As indicated by decision block 380, the system then awaits input from the user. The user may select a plot by clicking on one of the graphic curves in display 374 or 378 as determined at decision block 382. When this occurs the x, y location in each of the displayed spatial images 366, 368 and 370 is highlighted as indicated at process block 390. As explained above, the x, y position is known because it is stored in the field 356 of the memory array 350 for the selected plot voxel. In addition, when the user clicks on a selected graphic curve a CSF velocity spatial image and/or cumulative flow spatial image is displayed at 391 depending on whether a velocity curve or cumulative flow curve is selected. Also, the point at which the user clicks on the selected curve corresponds to a time, or cardiac phase, and this information is used to select the spatial image closest in time for display at 391.

The user may also select an x, y voxel location in one of the displayed spatial images 366,368 or 310 as indicated at decision block 392. When this occurs the corresponding graphic curves in the displayed plots 374 and 378 are highlighted as indicated at process block 394. This is accomplished by locating each illuminated voxel in the display array 350 having the selected x, y position in its field 356. This spatial-temporal mapping between the graphic curves and the spatial images effectively adds temporal information to the spatial images and spatial information to the temporal graphic curves.

The ability to relate temporal characteristics of individual voxels to spatial locations in the subarachnoid region is particularly useful in diagnosing Chiari patients. It has been discovered that the flow characteristics of CSF in high velocity "jets" during portions of the cardiac cycle are important in diagnosing Chiari I patients. The peak velocities in such jets is significantly higher in Chiari I and Chiari 0 patients than in normal subjects. This is determined by selecting CSF velocity curves that exhibit high peaks at some point in the cardiac cycle and observing that their voxels are clustered together in the spatial images. Another characteristic of Chiari I patients is the presence of a retrograde, or negative, CSF flow at the same time during the cardiac cycle as positive CSF flow out of the cranium (cephalad). This can be seen in the CSF velocity curves and related to jets of flow. Such jets nearly always exhibit substantially unidirectional flow in Chiari I and Chiari 0 patients during the entire cardiac cycle. This can be seen in the cumulative flow curves that indicate a substantial cumulative flow at the end of the cardiac cycle from voxels located in a jet. CSF flow in a subregion (usually a jet) in only one direction, or preponderantly in one direction during a cardiac cycle correlates highly with Chiari I and Chiari 0 disease.

It should be apparent to those skilled in the art that the present invention is applicable to the analysis of other flowing fluids in the body. For example, the invention may be used to examine the flow of blood in large arteries that are congested with plaque. Or, the invention may be employed to analyze the type and nature of blood flow through a patent forearm ovale. The patent forearm ovale is an opening between the right and left sides of the heart which normally closes at birth, but remains open for a certain percentage of the population and can present significant health problems.

In the Chiari malformation embodiment discussed above only one flow direction (along the spinal column) is of any clinical value. However, it should be apparent that other clinical applications may require the analysis of two or three flow directions. This is usually the case when analyzing blood flow in large vessels and in such cases the pulse sequence will need to be repeated to velocity encode along two or three different directions.

The invention claimed is:

1. A method for displaying a data set having spatial coordinates and a time coordinate, the steps comprising:
   a) displaying, on a display, a spatial image using data in the data set at a selected time;
   b) displaying temporal, graphic curves of the data in the data set as a function of time for locations in the spatial image;
   c) selecting a spatial location in the spatial image; and
   d) based on step c), automatically highlighting the displayed temporal graphic curves corresponding to the selected spatial location.

2. The method of claim 1 which includes:
   e) designating a point on one of the displayed temporal, graphic curves; and
   f) updating the displayed spatial image using the data at a time corresponding to the designated point on said one displayed temporal, graphic curve.

3. The method as recited in claim 1 which includes:
   g) selecting one of the displayed temporal, graphic curves; and
   h) based on step g), automatically highlighting the location in the spatial image which corresponds with the selected temporal, graphic curve.

4. A system for displaying a series of spatial images acquired over a time period, the combination comprising:
   first means for displaying one of said series of spatial images;
   second means for displaying a plurality of temporal graphic curves of corresponding voxel values in the series of images;
   means for linking each displayed temporal graphic curves to the corresponding voxel on the displayed spatial image; and
   which includes means for selecting a point on the displayed temporal graphic curves that corresponds to a time during the time period at which another one of the spatial images was acquired, and the first means for displaying is responsive to the selecting means to display the another one of the spatial images.

5. The system as recited in claim 4 which includes means for selecting a displayed temporal graphic curve, and means responsive to the selection and the linking means to indicate on the displayed spatial image the voxel corresponding to the selected temporal graphic curve.

6. The system as recited in claim 4 which includes means for selecting a voxel on the displayed spatial image, and means responsive to the selection and the linking means for indicating the corresponding displayed temporal graphic curve.

7. The system as recited in claim 6 in which the means for indicating highlights the corresponding displayed temporal graphic curve.

8. A method for studying the Chiari malformation in a subject, the steps comprising:
   a) acquiring a series of velocity images with a magnetic resonance imaging system that depict the flow of cerebrospinal fluid (CSF) through the subject's foramen magnum at successive times during a cardiac cycle;
   b) displaying, on a display, a spatial image depicting a flow parameter throughout the foramen magnum at a time during the cardiac cycle, the flow parameter being calculated from information in the acquired velocity images;

c) displaying a plurality of temporal graphic curve of a flow parameter, each temporal graphic curve indicating the value of a flow parameter at a voxel location in the spatial image throughout the cardiac cycle; and selecting a voxel location in the displayed spatial image and automatically highlighting the temporal graphic curves that corresponds with the selected voxel location.

9. The method as recited in claim 8 which includes selecting a time during the cardiac cycle and selecting for display in step b) the spatial image that depicts the flow parameters at the selected time.

10. The method as recited in claim 8 in which the flow parameter is cephalad CSF flow.

11. The method as recited in claim 8 in which the flow parameter is caudad CSF flow.

12. The method as recited in claim 8 in which the flow parameter is throughput.

13. The method as recited in claim 8 in which the flow parameter is cumulative flow.

14. The method as recited in claim 8 in which the flow parameter is flow velocity.

15. A computer system including a computer processor and a computer-readable storage medium having stored thereon instructions, that when accessed and executed by the computer processor, cause the computer processor to:

access a series of spatial images formed of a plurality of image voxels and acquired over a time period;

display at least one of the series of spatial images;

display a plurality of temporal, graphic curves depicted by plotting a parameter value associated with at least one of the series of spatial images as a function of at least a temporal component for each image voxel in the series of images;

link each displayed temporal, graphic curve to a corresponding voxel on the at least one displayed spatial image; and in response to a user selection of at least one of the displayed temporal, graphic curves, highlight spatial location in the at least one of the series of spatial images including a corresponding voxel to the user selection of at least one of the displayed temporal, graphic curves.

16. The computer system of claim 15 wherein the temporal, graphic curves are substantially free of spatial information apart from being linked to the corresponding voxel on the at least one displayed spatial image.

17. The computer system of claim 15 wherein the temporal component includes at least one of cerebral spinal fluid (CSF) flow velocity and cumulative flow.

18. The computer system of claim 15 further comprising creating a three-dimensional array to store, for each voxel, a value that indicates whether or not the voxel is to be illuminated as part of a temporal, graphic curve.

19. A method for studying the Chiari malformation in a subject, the steps comprising:

a) acquiring a series of velocity images with a magnetic resonance imaging system that depict the flow of cerebrospinal fluid (CSF) through the subject's foramen magnum at successive times during a cardiac cycle;

b) displaying, on a display, a spatial image depicting a flow parameter throughout the foramen magnum at a time during the cardiac cycle, the flow parameter being calculated from information in the acquired velocity images;

c) displaying a plurality of temporal graphic curves of a flow parameter, each temporal graphic curve indicating the value of a flow parameter at a voxel location in the spatial image throughout the cardiac cycle;

selecting a displayed temporal graphic curve, and automatically highlighting the corresponding voxel location in the displayed spatial image.

20. The method as recited in claim 19 which includes selecting a time during the cardiac cycle and selecting for display in step b) the spatial image that depicts the flow parameters at the selected time.

21. The method as recited in claim 19 in which the flow parameter is cephalad CSF flow.

22. The method as recited in claim 19 in which the flow parameter is caudad CSF flow.

23. The method as recited in claim 19 in which the flow parameter is throughput.

24. The method as recited in claim 19 in which the flow parameter is cumulative flow.

25. The method as recited in claim 19 in which the flow parameter is flow velocity.

* * * * *

UNITED STATES PATENT AND TRADEMARK OFFICE
CERTIFICATE OF CORRECTION

PATENT NO.         : 8,315,450 B2
APPLICATION NO.    : 11/280051
DATED              : November 20, 2012
INVENTOR(S)        : Mark F Quigley Page 1 of 1

It is certified that error appears in the above-identified patent and that said Letters Patent is hereby corrected as shown below:

Column 11, Claim 8, line 1, "curve" should be --curves--.

Signed and Sealed this
Twenty-ninth Day of January, 2013

David J. Kappos
*Director of the United States Patent and Trademark Office*